(12) United States Patent
Schmitz et al.

(10) Patent No.: US 11,744,938 B2
(45) Date of Patent: Sep. 5, 2023

(54) TITRATION FOR MEDICAL INFUSION DEVICES AND SYSTEMS

(71) Applicant: Medtronic, Inc., Minneapolis, MN (US)

(72) Inventors: Michael C. Schmitz, Prior Lake, MN (US); Dale F. Seeley, Spring Park, MN (US); Keith R. Hildebrand, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 17/001,192

(22) Filed: Aug. 24, 2020

(65) Prior Publication Data

US 2020/0384194 A1    Dec. 10, 2020

Related U.S. Application Data

(62) Division of application No. 13/953,108, filed on Jul. 29, 2013, now abandoned.

(51) Int. Cl.
| | |
|---|---|
| *A61M 5/142* | (2006.01) |
| *A61M 5/172* | (2006.01) |
| *A61M 5/168* | (2006.01) |
| *G16H 20/17* | (2018.01) |

(52) U.S. Cl.
CPC ...... *A61M 5/14248* (2013.01); *A61M 5/1723* (2013.01); *G16H 20/17* (2018.01); *A61M 5/14276* (2013.01); *A61M 5/16827* (2013.01); *A61M 2005/14208* (2013.01); *A61M 2205/3569* (2013.01); *A61M 2205/3592* (2013.01); *A61M 2205/50* (2013.01)

(58) Field of Classification Search
CPC ............ A61M 5/14248; A61M 5/1723; A61M 5/14276; A61M 5/16827; A61M 2005/14208; A61M 2205/3569; A61M 2205/3592; A61M 2205/50; A61M 2205/35; G16H 20/17
See application file for complete search history.

(56) References Cited

U.S. PATENT DOCUMENTS

| | | | |
|---|---|---|---|
| 5,389,078 | A | 2/1995 | Zalesky et al. |
| 6,010,483 | A * | 1/2000 | Spencer ................ A61M 5/172 604/151 |
| 6,231,560 | B1 | 5/2001 | Bui et al. |
| 7,303,549 | B2 | 12/2007 | Flaherty et al. |
| 7,828,771 | B2 | 11/2010 | Chiang et al. |

(Continued)

FOREIGN PATENT DOCUMENTS

| | | |
|---|---|---|
| WO | 00/047255 | 8/2000 |
| WO | 2003/011358 | 2/2003 |
| WO | 2007/147505 | 12/2007 |

OTHER PUBLICATIONS

Partial Search Report for PCT/US2014/047877 dated Oct. 28, 2014.

*Primary Examiner* — Lauren P Farrar
*Assistant Examiner* — Hamza A Darb
(74) *Attorney, Agent, or Firm* — Mueting Raasch Group

(57) ABSTRACT

Titration schemes are carried out by medical infusion devices, such as ambulatory or implantable infusion devices. The titration schemes carried out by infusion systems and devices may take into account patient side effects in controlling the rate at which a medicament is delivered from the devices of systems.

12 Claims, 10 Drawing Sheets

(56) References Cited

U.S. PATENT DOCUMENTS

| | | |
|---|---|---|
| 8,025,658 B2 | 9/2011 | Chong et al. |
| 8,048,040 B2 | 11/2011 | Kiani |
| 8,657,807 B2 | 2/2014 | Blomquist |
| 9,375,529 B2 | 6/2016 | Searle et al. |
| 10,092,691 B2 | 10/2018 | Searle et al. |
| 2002/0115933 A1* | 8/2002 | Duchon ............ A61M 5/14546 600/432 |
| 2003/0069318 A1 | 4/2003 | Dang et al. |
| 2008/0208173 A1 | 8/2008 | Lee et al. |
| 2009/0259176 A1 | 10/2009 | Yairi |
| 2012/0157920 A1 | 6/2012 | Flachbart et al. |

* cited by examiner

TITRATION FOR MEDICAL INFUSION DEVICES AND SYSTEMS

RELATED APPLICATIONS

This application is a divisional of U.S. patent application Ser. No. 13/953,108, filed on Jul. 29, 2013, which is hereby incorporated in reference in its entirety.

FIELD

This disclosure generally relates to, among other things, titration of dosing of medicaments delivered by medical infusion devices and systems and methods associated therewith.

BACKGROUND

Medical infusion devices and systems are employed to infuse liquid medicament compositions to patients to treat a number of diseases. For example, ambulatory infusion systems configured to deliver insulin subcutaneously to patients are used to treat diabetes. Implantable infusion devices configured to deliver baclofen or morphine intrathecally are used to treat spasticity or pain. However, for these or other existing or proposed therapies employing medical infusion devices, titrating the initial dosage can be difficult or time consuming and may require the patient to visit a health care provider multiple times until an appropriate maintenance dose is achieved.

Regardless of the route of administration, it is often desirable to deliver a low dose of a medicament to a patient and increase the dose over time in an effort to avoid side effects of the medicament, while maximizing efficacy. For some medicaments, it may take many months to ramp up dosage to a desired level. Typically, a health care provider assists the patients with ramping up the dosage and often controls the dosage at various stages of dose escalation. This allows the health care provider to closely monitor patient progress and assist the patient in determining whether the patient is experiencing side effects associated with the medicament. However, such a process may require the patient to visit a health care provider many times during the dose escalation period.

SUMMARY

This disclosure describes, among other things, titration schemes incorporated into medical infusion devices, such as ambulatory or implantable infusion devices, that account for patient side effects. Because such systems and devices account for patient side effects, the devices may automatically escalate dosing during titration, which may allow titration to occur more quickly or may reduce the number of times the patient visits a health care provider during a dose escalation titration procedure.

In embodiments, a medical infusion device includes a reservoir for housing a liquid composition comprising a medicament and a pump mechanism configured to drive the liquid composition from the reservoir to a patient. The infusion device also includes input apparatus configured to receive input indicative of a patient side effect of the medicament and control electronics operably coupled to the pump mechanism and to the input apparatus. The control electronics are configured to:
(a) cause the pump mechanism to drive the liquid composition from the reservoir to the patient for a predetermined period of time at a rate increased relative to a preceding rate if no input indicative of a patient side effect has been received during a period of time in which the pump mechanism drove the liquid composition from the reservoir to the patient at the preceding rate; and
(b) repeat step (a) until a maximum predetermined rate has been achieved or until input indicative of a patient side effect is received.

In embodiments, a medical infusion system includes a first device having first control electronics and having, or configured to operably couple to, (i) a first reservoir for housing a liquid composition comprising a medicament, (ii) a first pump mechanism configured to drive the liquid composition from the first reservoir to a patient, and (iii) first input apparatus configured to receive input indicative of a patient side effect of the medicament. The first control electronics are operably coupled to the first pump mechanism and to the first input apparatus. The first control electronics are configured:
(a) to cause the first pump mechanism to drive the liquid composition from the first reservoir to the patient for a predetermined period of time at a rate increased relative to a preceding rate if no input indicative of a patient side effect has been received during a period of time in which the first pump mechanism drove the liquid composition from the first reservoir to the patient at the preceding rate; and
(b) to repeat step (a) until a maximum predetermined rate has been achieved or until input indicative of a patient side effect is received.

The system further includes a second device having second control electronics and having, or configured to operably couple to, (i) a second reservoir for housing a liquid composition comprising a medicament, (ii) a second pump mechanism configured to drive the liquid composition from the second reservoir to a patient, and (iii) second input apparatus configured to receive input indicative of a patient side effect of the medicament. The second control electronics are operably coupled to the second pump mechanism and to the second input apparatus. The second control electronics are configured:
(c) to cause the second pump mechanism to drive the liquid composition from the second reservoir to the patient for a predetermined period of time at a rate increased relative to a preceding rate if no input indicative of a patient side effect has been received during a period of time in which the second pump mechanism drove the liquid composition from the second reservoir to the patient at the preceding rate; and
(d) to repeat step (c) until a maximum predetermined rate has been achieved or until the second control electronics determine that input indicative of a patient side effect is received.

The first and second devices are configured to be employed by the patient sequentially such that the second device is employed by the patient to deliver the medicament after the first device is no longer being used to deliver the medicament. The first device is configured to transmit to the second device data regarding the last rate at which the first pump mechanism was configured to drive the liquid composition from the first reservoir to the patient. The second control electronics are configured to set the last rate of the first pump mechanism as the initial rate of the second pump mechanism in step (c).

In embodiments, a method of titrating dosage of a medicament from a medical infusion device is described. The medical infusion device has a reservoir for housing a liquid composition comprising a medicament and pump mechanism for driving the liquid composition from the reservoir to a patient. The method is carried out by the medical infusion device and includes:
  (a) determining whether input indicative of a patient side effect has been received;
  (b) causing the pump mechanism to drive the liquid composition from the reservoir to the patient for a predetermined period of time at a rate increased relative to a preceding rate if a determination is made that no input indicative of a patient side effect has been received during a period of time in which the pump mechanism drove the liquid composition from the reservoir to the patient at the preceding rate; and
  (c) repeating steps (a) and (b) until a maximum predetermined rate has been achieved or until a determination is made that input indicative of a patient side effect has been received.

In embodiments, a method of titrating dosage of a medicament from a medical infusion system sequentially employing first and second devices to deliver the medicament to a patient such that the second device replaces the first device to deliver the medicament to the patient after the first device is no longer employed to deliver the medicament is described. The method includes:
  (1) employing the first device to:
    (a) determine whether input indicative of a patient side effect has been received;
    (b) cause a liquid composition comprising the medicament to be delivered to a patient for a predetermined period of time at a rate increased relative to a preceding rate if a determination is made that no input indicative of a patient side effect has been received during a period of time in the liquid composition was driven at the preceding rate; and
    (c) repeat steps (a) and (b) until a maximum predetermined rate has been achieved or until the determination is made that input indicative of a patient side effect has been received or until the first device is replaced by the second device; and
  (2) replacing the first device with the second device, transmitting data to the second device regarding the last rate at which the first device caused the liquid composition to be delivered to the patient, and transmitting data to the second device regarding whether input indicative of a patient side effect has been received; and
  (3) employing the second device to: (d) cause the liquid composition comprising the medicament to be delivered to the patient at the last rate at which the first device caused the liquid composition to be delivered to the patient if the transmitted data indicates that the maximum predetermined rate has been achieved or that input indicative of a patient side effect has been received; or
    (e) if the transmitted data indicates that the maximum predetermined rate has not been achieved and that no input indicative of a patient side effect has been received,
      (i) cause the liquid composition comprising the medicament to be delivered to the patient for a predetermined period of time at the last rate at which the first device caused the liquid composition to be delivered to the patient or a rate increased relative to the last rate at which the first device caused the liquid composition to be delivered to the patient;
      (ii) determine whether input indicative of a patient side effect has been received;
      (iii) cause the liquid composition comprising the medicament to be delivered to the patient for a predetermined period of time at a rate increased relative to a preceding rate if a determination is made that no input indicative of a patient side effect has been received during a period of time in the liquid composition was driven at the preceding rate; and
      (iv) repeat steps (ii) and (iii) until a maximum predetermined rate has been achieved or until the determination is made that input indicative of a patient side effect has been received.

One or more embodiments of the devices, systems or methods described herein provide one or more advantages over prior devices, systems or methods. As indicated above, the methods, devices and systems described herein may allow titration to occur more quickly or may reduce the number of times the patient visits a health care provider during a dose escalation titration procedure. These and other advantages will be readily understood from the following detailed description.

Figure 1:
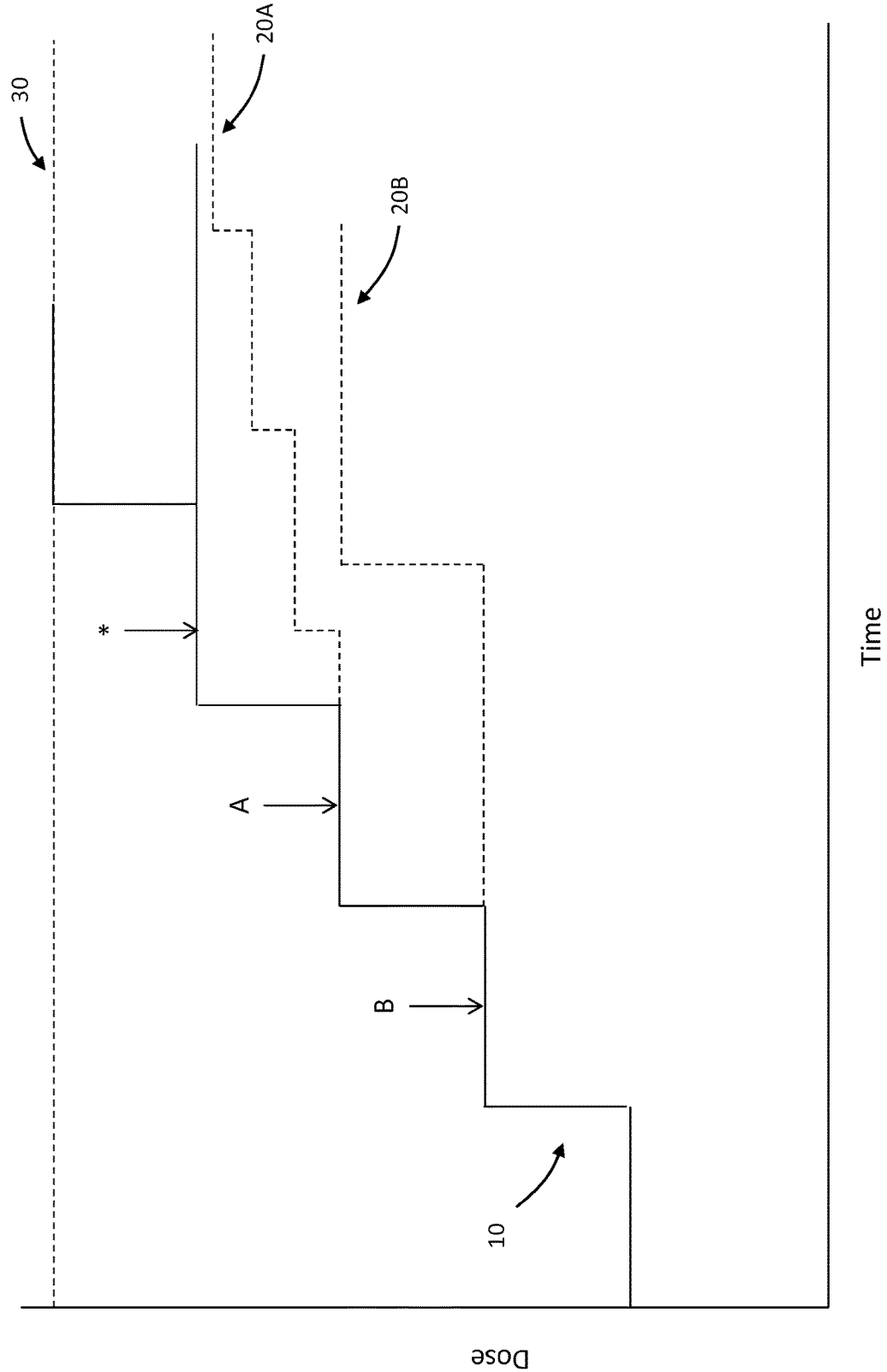
FIG. 1 is a schematic drawing of an embodiment of a titration scheme and subschemes that may be employed in accordance with the teachings presented herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, "input indicative of a patient side effect of a medicament" is data received by an infusion device or system, or component thereof, regarding whether a patient is or has experienced a side effect associated, or believed to be associated, with the medicament. The data may also include information regarding severity of the side effect, the nature of the side effect, or the like.

As used herein, a "predetermined" value is a value that is determined prior to the time in which it is employed. The value may be based on data obtained earlier in time to when the value is employed, may be a value placed in memory prior to use, or the like.

This disclosure generally relates to, inter alia, titration schemes carried out by medical infusion devices, such as ambulatory or implantable infusion devices. The titration schemes carried out by infusion systems and devices, in many embodiments, account for patient side effects, which may allow titration to occur more quickly or may reduce the number of times the patient visits a health care provider during a dose escalation titration procedure.

The titration schemes described herein may be employed by any suitable medical infusion device. In various embodiments, external infusion devices or systems, implantable infusion devices or systems, or ambulatory infusion devices or systems are employed. Preferably, the infusion devices or systems are implantable or ambulatory. As used herein, ambulatory, with regard to an infusion device, means that the infusion device is wearable or attachable to a patient such that the patient can readily move about while wearing the device or while the device is attached to the patient. Ambulatory pumps may be configured to deliver medicaments transdermally, transcutaneously, or the like. Ambulatory pumps include patch pumps that are configured to adhere to a patient's skin. Examples of ambulatory pumps include Medtronic MiniMed's PARADIGM insulin pumps, Animas Corporation's VIBE and ONE TOUCH PING insulin pumps, Insulet Corporations OMNIPOD system, Roche Insulin Delivery Systems Inc.'s ACCU-CHEK COMBO system, and Tandem Diabetes Care's TSLIM insulin pump. One example of a suitable patch pump is described in U.S. Pat. No. 8,025,658 entitled "ADHESIVE PATCH SYSTEMS AND METHODS" issued on Sep. 27, 2011. Examples of suitable implantable infusion devices include Medtronic Inc.'s SYNCHROMED infusion pumps, Arrow International's INFUSAID pump, and Codman and Shurtleff, Inc.'s CODMAN 3000 drug pump. The devices and systems described above may be readily modified to employ titration schemes described herein and may be used to deliver any suitable medicament for any suitable therapeutic purpose.

Referring now to FIG. 1, an example of schematic stepwise dose escalation scheme 10 is depicted. At predetermined points in time the dose is escalated by a predetermined amount; the dose is held constant for a predetermined period of time before the next escalation; and so on. The maximum dose 30 may be a dose determined by a healthcare provider based on knowledge of maximum recommended doses for the particular medicament, based on patient history which may include other medications the patient is taking, or the like. A dose escalation scheme will typically include a maximum dose 30 rather than allowing the dose to increase indefinitely.

For purposes of illustration, a time at which a patient may experience a side effect is depicted by the arrow with the * above the arrow in FIG. 1. Once input is received by an infusion device that the patient is experiencing a side effect, the dose is decreased. By way of example, the dose may be decreased to the immediately preceding dose at which the patient did not experience the side effect (indicated by arrow with "A" over the arrow) or may be decreased to the dose two time periods prior to the dose at which the side effect occurred (indicated by the arrow with the "B" over the arrow). Of course, the dose may be decreased by any suitable amount. The amount by which the dose is decreased may be based on the severity of the side effect, the medical judgment or experience of a health care provider regarding the particular patient, or the like.

In some cases, after the dose is decreased following a side effect, it may be desirable to sub-titrate to increase dosing in a manner different from the original scheme 10. Two examples of sub-titration schemes 20A, 20B are shown in FIG. 1. Scheme 20A increases dosages by a predetermined amount smaller than with the original scheme 10 to allow fine tuning of the titration. Scheme 20B maintains dosages at predetermined levels for longer periods of time than with the original scheme 10. Of course any suitable combination of time period change or dose increment change may be employed in a sub-titration scheme.

While FIG. 1 depicts a regularly repeating step-wise scheme, any suitable titration scheme may be employed. Preferably, the scheme employs delivery of a predetermined constant rate for a predetermined period of time rather than a continuously gradual increase in dose. Holding a dose steady over a predetermined period of time allows time for systemic effects of a given dose on the patient to be analyzed, which allows time to determine whether the particular dose results in side effects.

While FIG. 1 depicts a dosing scheme 10 in which the time period between each dose escalation is the same and where the escalation in dose at each change in dose is the same, the time period between each dose escalation need not be the same and the escalation at each change in dose need not be the same. For example, the overall dosing scheme may have shorter times between dose escalations or greater increases in dose earlier or later in the scheme (e.g., at doses where the patient is less likely to experience side effects with the given medicament) or longer times or smaller increments earlier or later in the scheme (e.g., at doses where the patient is more likely to experience side effects with the given medicament).

In embodiments, a predetermined time between dose changes is from about twelve hours to about one week. In some embodiments, a predetermined time between dose changes is about three days. Often ambulatory infusion devices require movement of the position of the device or associated cannula with respect to the patient every three days to avoid skin complications. It may be advantageous to tie the dose change interval with movement of the device or cannula. In some instances, rather than moving the device or cannula at predetermined intervals, the device or cannula is replaced by another device or cannula at a different position on the patient's body than where the first device or cannula was positioned. With some infusion devices, a reservoir is refilled at regular intervals, and it may be advantageous to tie the dose change interval with refilling of the reservoir. In the case of certain patch pumps, the reservoir is refilled about every three days. The predetermined amount of time for refilling the reservoir or setting the dose change interval will depend on the medicament that will be delivered to the patient as well as the disease or condition being treated. Other factors, such as a particular patient's sensitivity to the medicament or the pump being positioned at a site on the patient's body may result in more frequent changes of the pump position.

The titration schemes or methods described herein may be employed at any time where it is desired to change dose. In many circumstances, the titration will occur at the time of initiation of therapy to establish a safe and effective maintenance dose.

Figure 2:
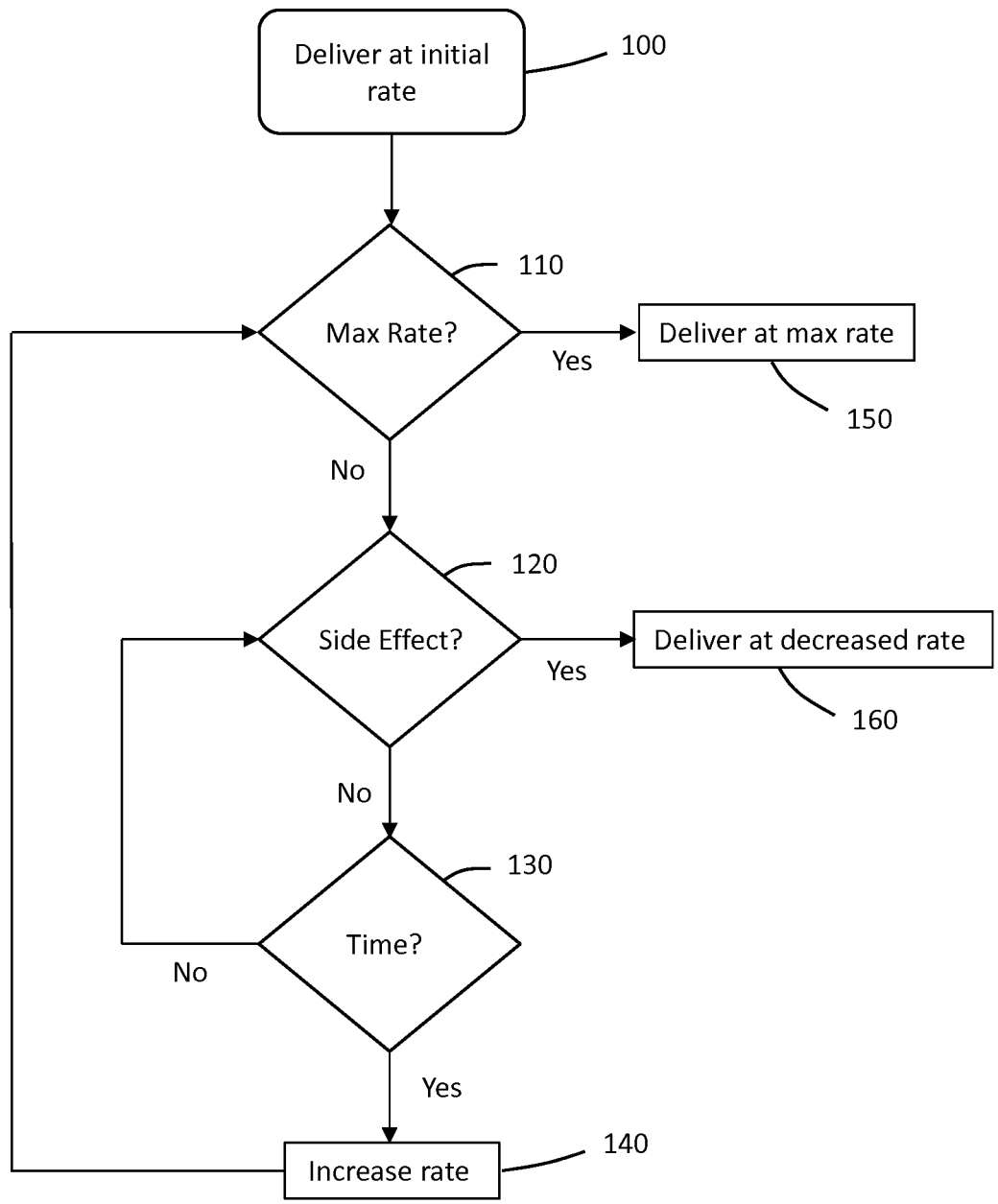
FIGS. 2-8 are flow diagrams of embodiments of methods that may be employed in accordance with the teachings presented herein.

Referring now to FIGS. 2-6, some examples of methods for carrying out titration schemes are presented. As shown in FIG. 2, an infusion device may be configured to deliver a liquid composition at an initial rate (100), which corresponds to an initial dose of the medicament. The method includes determining whether the maximum rate (e.g., rate 30 in FIG. 1) has been achieved (110). Of course, the maximum rate should not be achieved with initial dosing (100), but may be achieved after several iterations of dose increments. If the maximum rate is not achieved, an infusion device may determine whether any input indicative of a patient side effect has been received (120). Of course the side effect determination (120) may be made prior to the maximum rate determination (110). If the infusion device receives no input regarding a patient side effect, a determination as to whether the time period for a particular dose has expired (130) may be made. If the time period has expired (and if there is no side effect and if the maximum dose has not been reached), the pump may increase the rate at which the liquid composition comprising the medicament is delivered by a predetermined amount (140). Steps 110, 120, 130, 140 may be repeated until the maximum rate has been achieved or a side effect occurs. If the maximum rate is achieved, the infusion device may continue to deliver the composition comprising the medicament at the maximum rate (150). If the infusion device received input indicative of a patient side effect, the infusion device may deliver the composition comprising the medicament at a predetermined rate decreased relative to the rate at which the side effect occurred (160).

Figure 3:
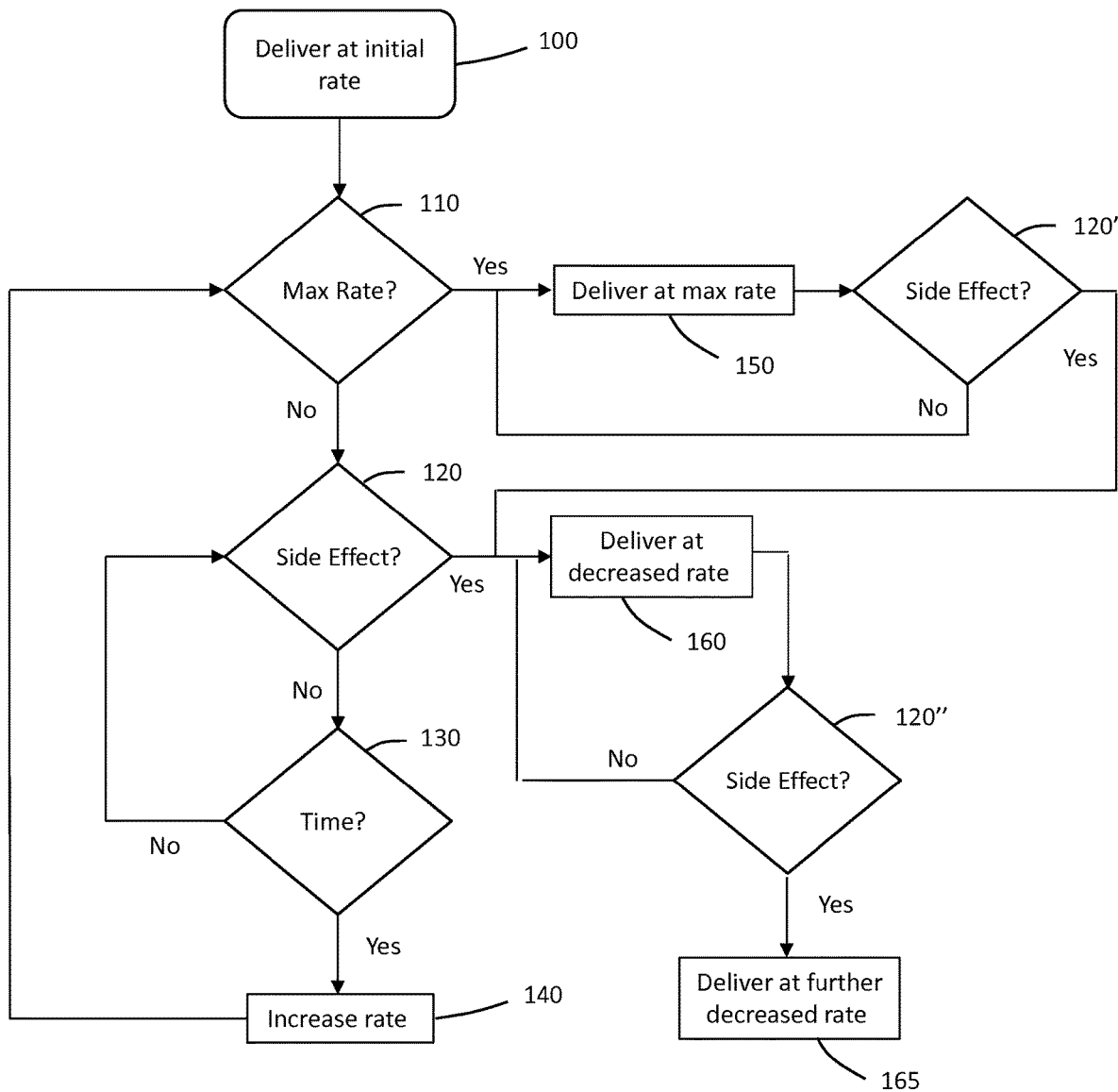

Many of the steps in FIG. 3 are the same or similar to the steps in FIG. 2. Reference is made to the discussion regarding FIG. 2 for those steps that are not specifically discussed with regard to FIG. 3. As shown in FIG. 3, it may be desirable to continue to monitor side effects even if the maximum rate is initially achieved without side effects. That is, a determination may be made as to whether the infusion device has received input indicative of a patient side effect (120') after the maximum rate/dose has been achieved and delivered (150). If no indication is received regarding a patient side effect, the pump may continue to deliver at the maximum rate (150). However, if the infusion device receives input indicative of a side effect, the pump may deliver the medicament at a decreased rate (160), preferably at a rate at which side effects were not observed. As further shown in FIG. 3, it may also be desirable to continue to monitor side effects even after the dosage has been decreased to a dose that previously did not result in a side effect. That is, a determination may be made as to whether the infusion device has received input indicative of a patient side effect (120") after the pump has decreased the rate of medicament delivery (160). If no indication is received regarding a patient side effect at the decreased rate, the pump may continue to deliver at the decreased rate (160). However, if the infusion device receives input indicative of a side effect, the pump may deliver the medicament at a further decreased predetermined rate (165). Additional iterations of checking for side effect input and rate reduction may be employed as desired.

Figure 4:
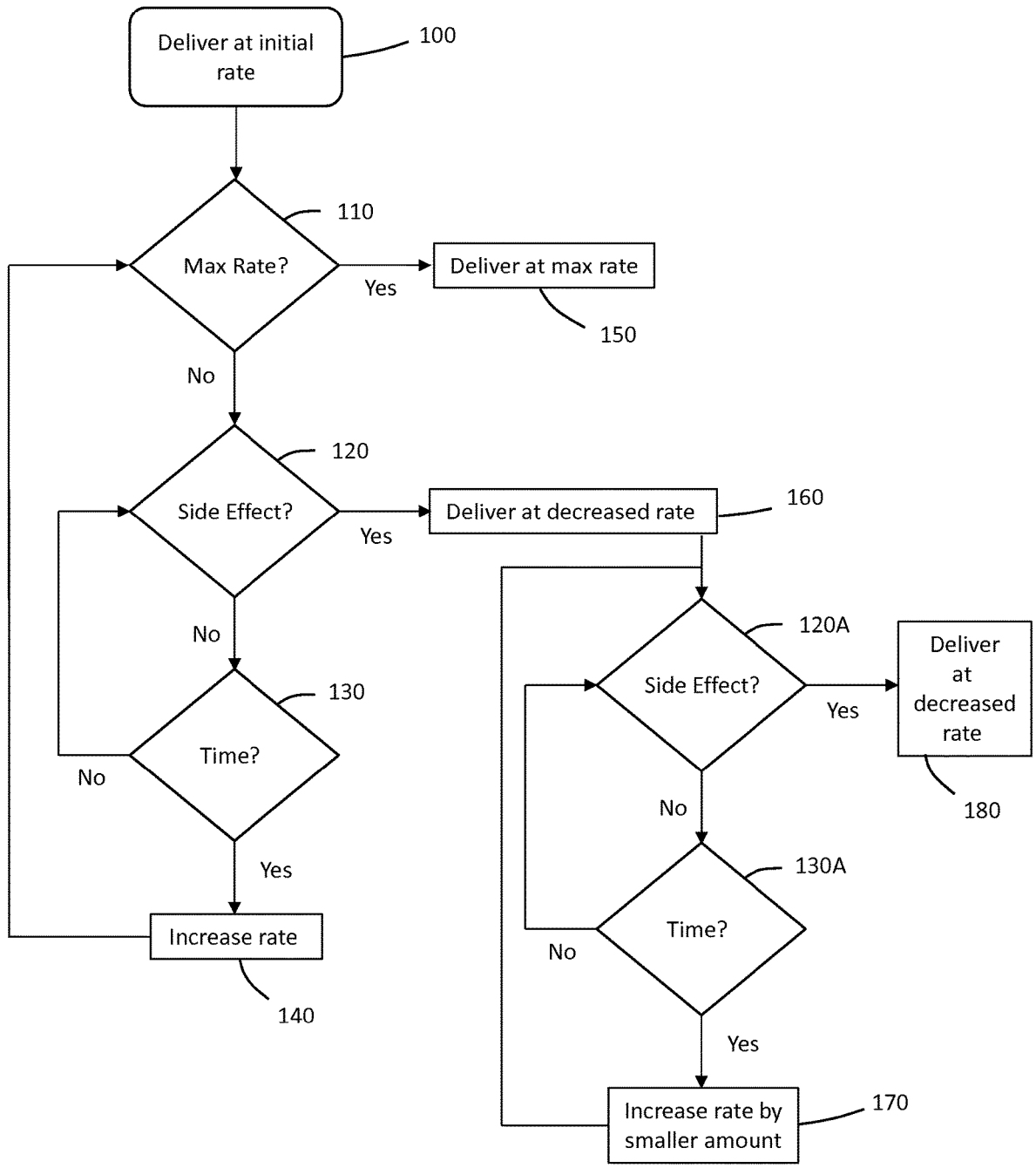

Many of the steps in FIG. 4 are the same or similar to the steps in FIGS. 2-3. Reference is made to the discussion regarding FIGS. 2-3 for those steps that are not specifically discussed with regard to FIG. 4. While not all the steps in FIG. 3 are included in the flow diagram of FIG. 4, it will be understood that those omitted steps may be readily included and are contemplated herein. In FIG. 4, an example of a method for sub-titration (e.g., titration scheme 20A in FIG. 1) is shown. As shown, delivery at a decreased rate (160) after side effect detection (120) may occur for some predetermined amount of time before sub-titration begins. If the infusion device has received no input indicative of side effects (e.g., the patient continues to be side effect free at the decreased dose) and the predetermined time has passed (130A), the infusion device at step 170 may increase the rate of delivery of the medicament by a predetermined amount smaller than an increment in step 140. A determination may be made as to whether the infusion device received input indicative of a patient side effect (120A). If the device receives input indicative of a side effect, the device may deliver the medicament at a decreased rate (180), which may be the same or different than the rate delivered at step 160, preferably at a rate that was previously determined to be side effect free. If no side effects are observed (120A) and the predetermined time period for a given dosage has passed (130A), the infusion device may again increase the rate of delivery by an amount smaller than the original titrate scheme (170).

Figure 5:
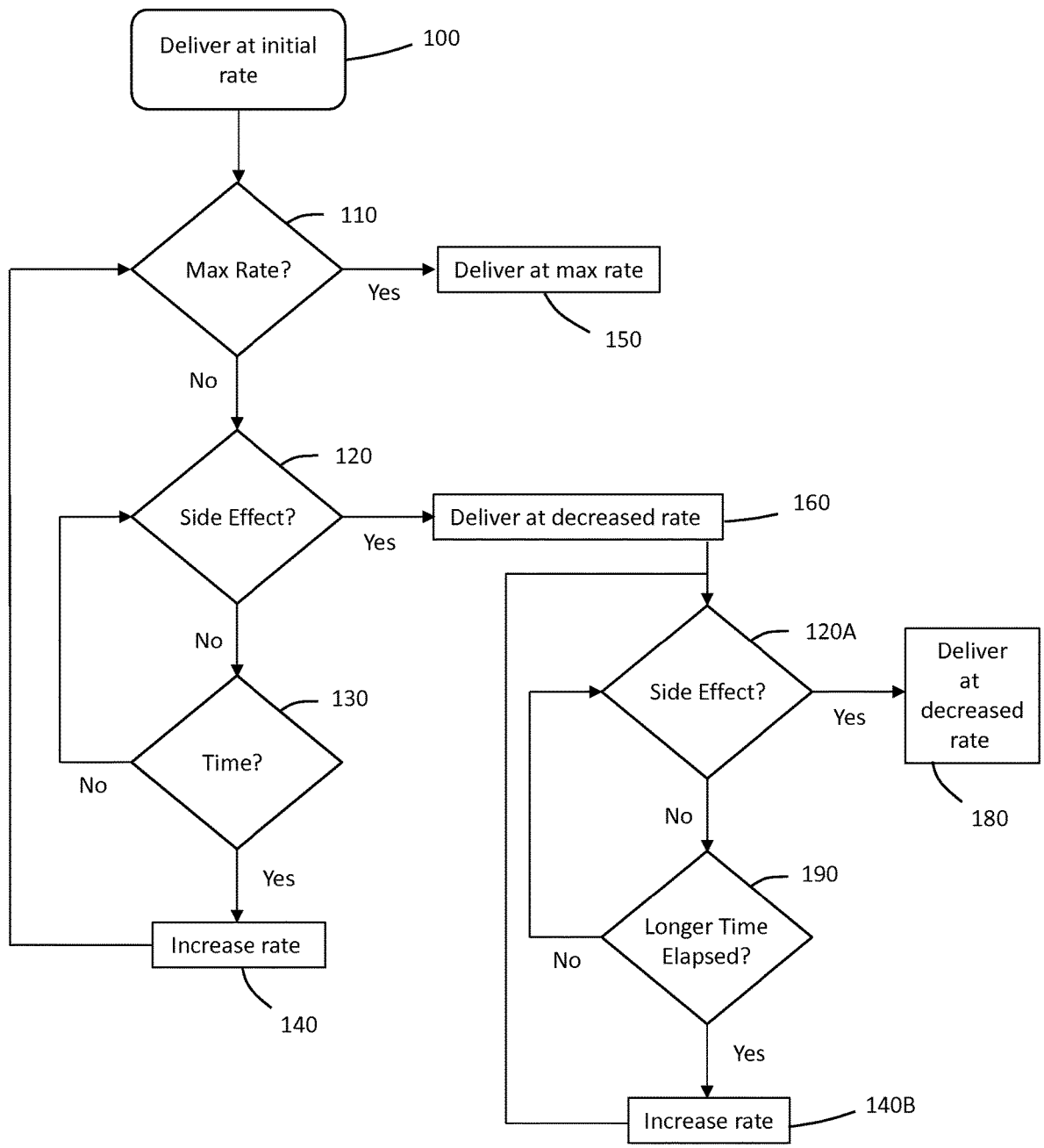

Many of the steps in FIG. 5 are the same or similar to the steps in FIGS. 2-4. Reference is made to the discussion regarding FIGS. 2-3 for those steps that are not specifically discussed with regard to FIG. 5. While not all the steps in FIG. 3 are included in the flow diagram of FIG. 5, it will be understood that those omitted steps may be readily included and are contemplated herein. In FIG. 5, an example of a method for sub-titration (e.g., titration scheme 20B in FIG. 1) is shown. As shown, delivery at a decreased rate (160) after side effect detection (120) may occur for some predetermined amount of time before sub-titration begins. If the infusion device has received no input indicative of side effects (e.g., the patient continues to be side effect free at the decreased dose) and the predetermined time has passed (190), the infusion device may increase the rate of delivery of the medicament (140B), which may be an increment the same or similar to increment at step 140. A determination may be made as to whether the infusion device received input indicative of a patient side effect (120A). If the device receives input indicative of a side effect, the device may deliver the medicament at a decreased rate (180), which may be the same or different than the rate delivered at step 160, preferably at a rate that was previously determined to be side effect free. If no side effects are observed (120A) and the predetermined time period for a given dosage has passed (190), which time period is greater than the time period in step 130, the infusion device may again increase the rate of delivery (140B).

Figure 6:
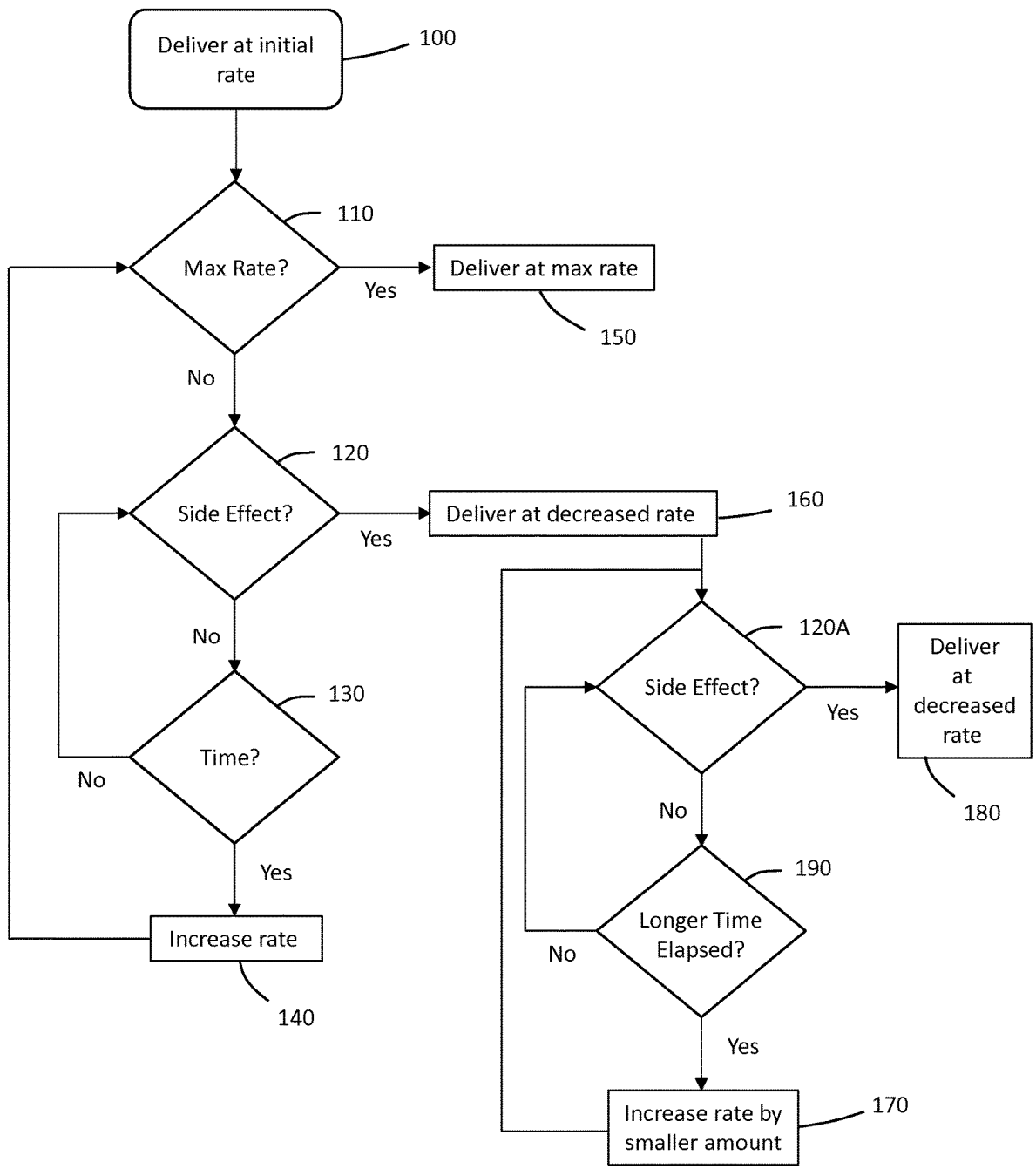

FIG. 6 depicts a method that incorporates aspects of the methods depicted in FIGS. 4-5. Like with FIGS. 4-5, many of the steps in FIG. 6 are the same or similar to the steps in FIGS. 2-3. Reference is made to the discussion regarding FIGS. 2-5 for those steps that are not specifically discussed with regard to FIG. 6. FIG. 6 depicts an embodiment where sub-titration with smaller dose increments (170) relative to step 140 and longer time periods (190) relative to step 130 are employed.

Figure 7:
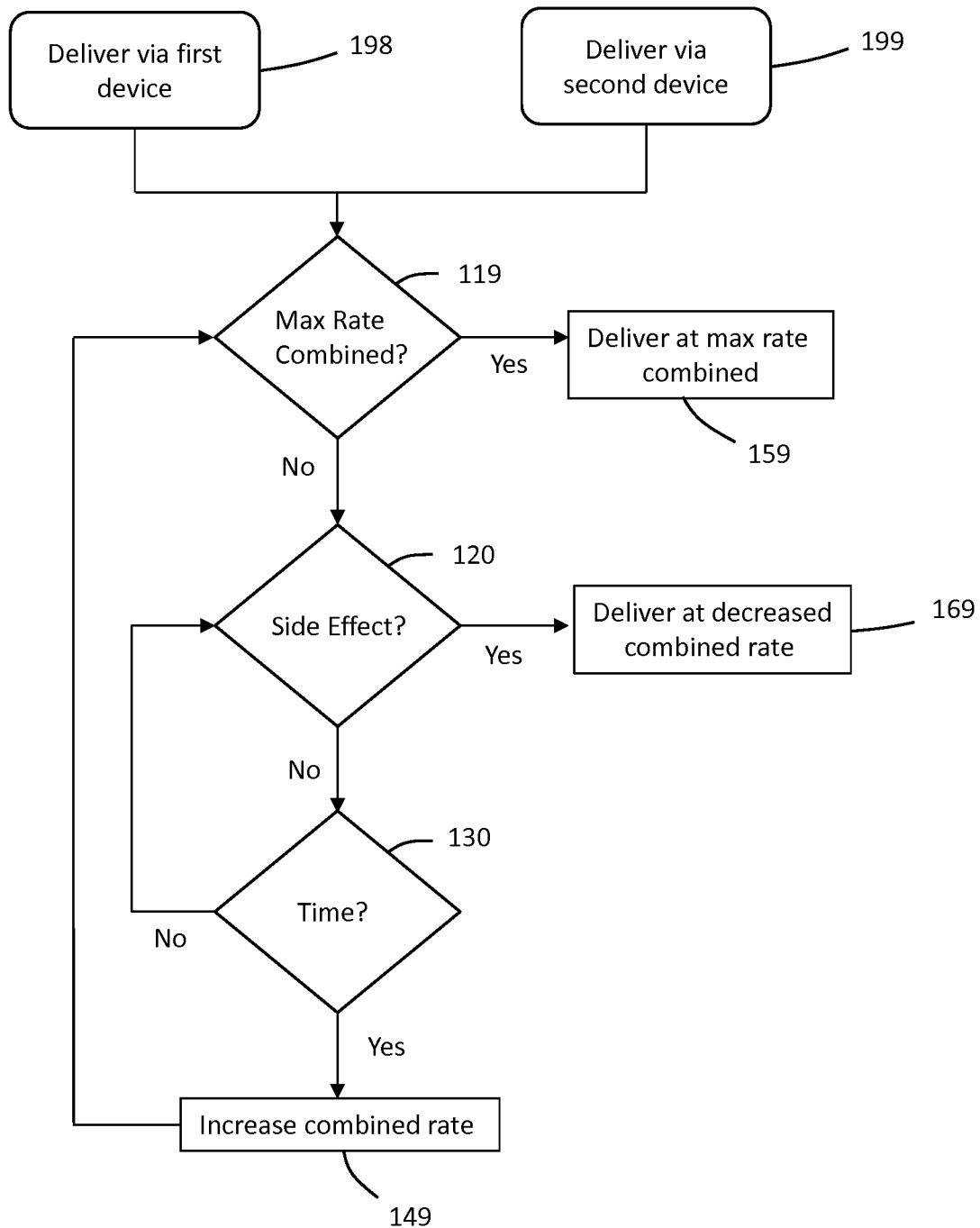
Figure 8:
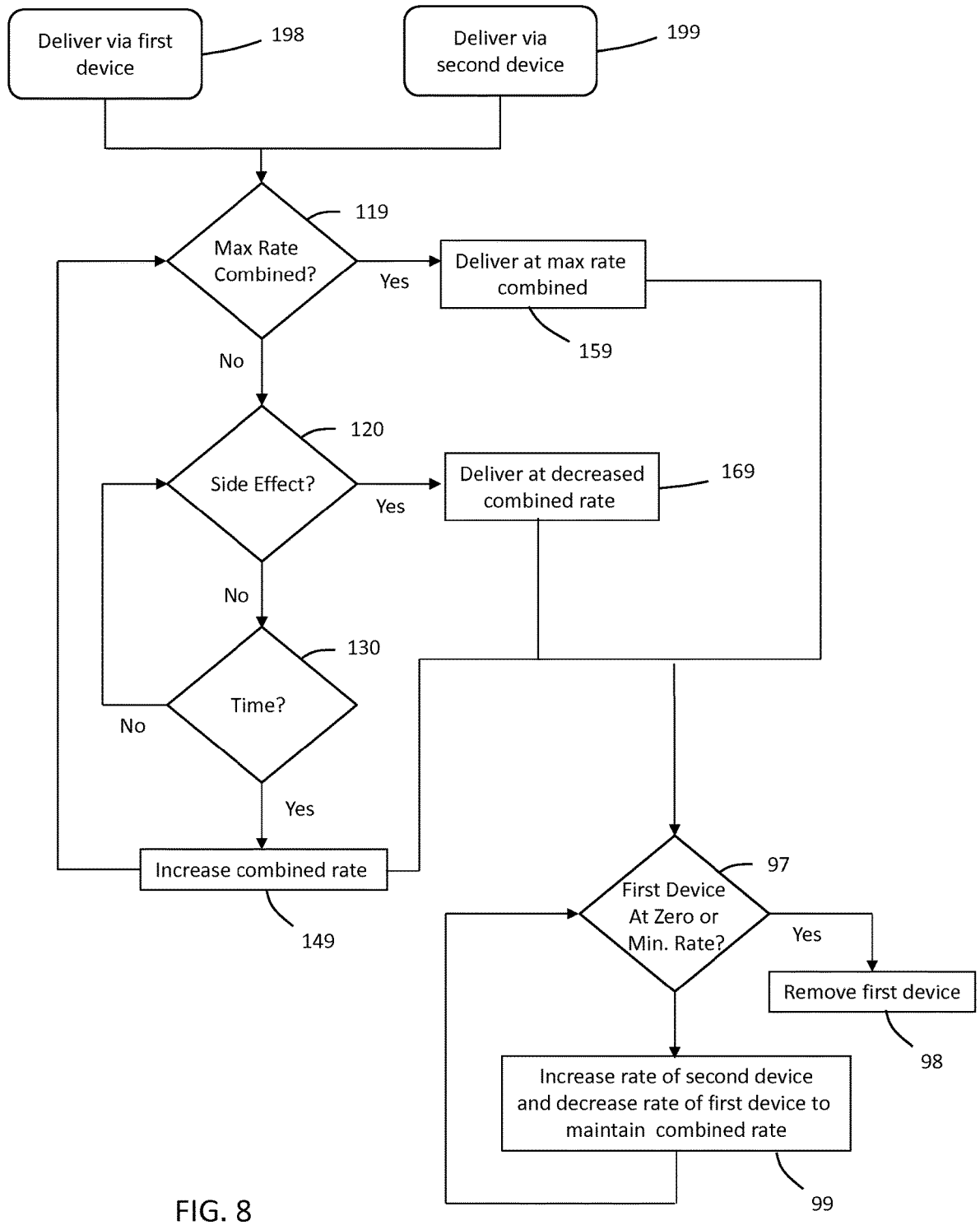

Referring now to FIGS. 7-8, embodiments where two or more infusion devices, each device comprising: control electronics and having, or configured to operably couple to, (i) a pump mechanism configured to drive the liquid composition from the a reservoir to a patient, and (ii) an input apparatus configured to receive input indicative of a patient side effect of the medicament, wherein the control electronics of each device are operably coupled to its respective pump mechanism and input apparatus, are at least for some period of time simultaneously used to deliver a medicament to a patient are presented. Such embodiments may include, for example, delivery from a first infusion device and a second infusion device. In the depicted methods, therapy is coordinated, and during the period of time where the infusion devices are simultaneously delivering medicament to the patient the combined rate at which the two or more devices deliver medicament to the patient are controlled by the respective control electronics of each device. At some time prior to or during the time of simultaneous delivery from two or more infusion devices, the devices are in communication with each other and therapy is coordinated so that the devices may operate at an appropriate combined rate to deliver an appropriate dose of medicament to the patient. The devices may communicate with each other directly through any form of wired or wireless communication (e.g., as discussed below with regard to FIG. 12) or may communicate through a third device. The depicted methods illustrate embodiments where first and second infusion devices are simultaneously delivering medicament to the patient.

As shown in FIG. 7, the pump mechanism of the first infusion device causes the delivery of medicament to the patient at a first predetermined rate (198) and the pump mechanism of the second infusion device causes delivery of medicament to the patient from the second infusion device at a second predetermined rate (199), where the first and second predetermined delivery rates are chosen so that the combined rate of the two devices is less than or equal to a predetermined maximum rate of delivery. A determination is made by the control electronics of the first infusion device using information obtained from the second infusion device (or from control electronics of an auxiliary device that is in communication with the first and second infusion devices) as to whether the combined delivery rates of the first and second infusion devices equal the maximum rate of delivery (119). If the maximum rate is achieved, the control electronics from the first infusion devices transmits the information to the control electronics from the second infusion device (or control electronics from the auxiliary device transmits data to the first and second devices) and the control electronics of each infusion device cause the respective pump mechanism of the device to continue to deliver medicament to the patient at the combined delivery rate that equals the maximum rate (159). If the maximum rate is not achieved, a determination may be made as to whether either of the two devices has received input indicative of a patient side effect (120), which decision may occur before or after the determination regarding maximum rate. If a side effect is determined to have occurred, the combined rate of delivery of the two devices may be decreased by a predetermined amount (169) by decreasing one or both of the first or second delivery rates. If no side effect is detected, a determination is made as to whether a predetermined period of time has elapsed since the beginning of combined delivery from the first and second devices at a predetermined rate (130). If the time period has elapsed (and the maximum rate has not been achieved and no side effect has occurred), the combined rate of delivery of the first and second devices may be increased (149). An increase in combined rate of delivery may constitute an increase in the rate of delivery from the first device, an increase in the rate of delivery from the second device, or an increase in rate in delivery from both the first and second devices. Similarly, a decrease in combined rate of delivery may constitute a decrease in the rate of delivery from the first device, a decrease in the rate of delivery from the second device, or a decrease in rate in delivery from both the first and second devices. The titration schemes described above may be applied when two infusion devices are simultaneously delivering medicament to a patient by increasing or decreasing the combined rate of delivery of the devices as shown in FIGS. 2-6 for increasing or decreasing the delivery rate of a single device.

Referring now specifically to FIG. 8, an embodiment of a method in which the second device is configured to eventually replace the first device in delivering the medicament to the patient is shown. Regardless of the combined rate of delivery (e.g. delivery at a rate of step 159, a rate of step 169, or a rate of step 149), the rate of delivery of medicament from the second device may be increased to compensate for a decrease in rate from the first device to maintain the combined rate (99). Total replacement of the first device by the second device may occur over several iterations of increasing the rate of delivery from the second device by a predetermined amount and decreasing the rate of delivery from the first device by a predetermined amount (while maintain the desired combined rate). When the first device is no longer delivering medicament or the rate of delivery has decreased below a predetermined threshold (97), the first device may be removed (98) and the second device will deliver at a rate to maintain therapy. The titration schemes described above and illustrated in FIGS. 2-6 may be applied to the delivery of medicament by the second device after the first device has been removed.

Any of the methods or titration schemes may be programmed into computer-readable media for use in, or incorporated in, a medical infusion pump. Preferably, the computer readable media is non-transitory. Computer readable media may be executable by control electronics of a medical infusion device to cause the device to carry out the methods or titration schemes described above or variations thereof.

Figure 9:
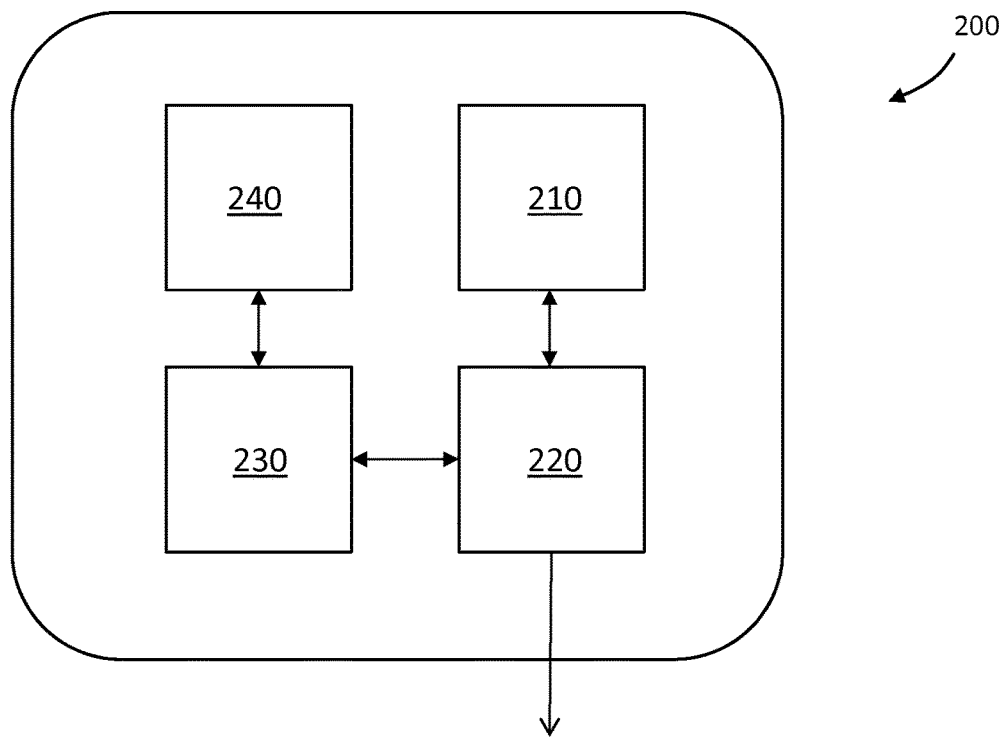
FIG. 9 is a schematic block diagram showing some components of an embodiment of a medical infusion device.

Referring now to FIG. 9, a schematic block diagram showing some components of an embodiment of a medical infusion device 200 are shown. The infusion device 200 includes a reservoir 210 for housing a liquid composition comprising a medicament. The reservoir 210 is operably coupled to a pump mechanism 220 configured to drive the liquid composition from the reservoir 210 to an outlet of the device 200 for delivery to a patient. While pump mechanism 220 is shown downstream of reservoir 210, pump mechanism 220, or components thereof (such as propellant, biasing mechanism, or the like) may be upstream of reservoir 210. Typically, when components of pump mechanism 220 are upstream of reservoir 210, other components of pump mechanism 220, such as valves, flow restrictors, rollers, or the like, are downstream of the reservoir. The device 200 typically is operably couplable to a catheter, cannula or other tubing (not shown) such that the catheter, cannula or tubing is in communication with reservoir or pump mechanism and configured to deliver the liquid composition from the reservoir to the patient.

Still referring to FIG. 9, the pump mechanism 220 is operably couplable to control electronics 230, which are configured to control the rate at which the pump mechanism 220 drives the liquid composition from the reservoir 210. Control electronics 230 may include a processor, memory, user interface, timer, clock or counter, power sources or the like. Control electronics 230 may include any suitable processor, such as one or more microprocessors, DSPs, ASICs, FPGAs, programmable logic circuitry, or the like, and the functions attributed to the processor herein may be embodied as hardware, firmware, software or any combination thereof. Memory may store instructions that cause the processor to provide the functionality ascribed to a system or device described herein, and may store information used by the processor to provide the functionality ascribed to a system or device described herein. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A power source may deliver operating power to components of a system or apparatus described herein. Power source may be an AC or DC power source, such as a battery and a power generation circuit to produce the operating power.

Methods described in this disclosure, including those attributed to devices or systems, or various constituent components, may be implemented, at least in part, in hardware, software, firmware or any combination thereof. For example, various aspects of the methods may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices.

When implemented in software, the functionality ascribed to the systems, apparatuses and methods described in this disclosure may be embodied as instructions on a computer-readable medium such as RAM, ROM, NVRAM, EEPROM, FLASH memory, magnetic data storage media, optical data storage media, or the like. Such computer-readable medium is non-transitory. The instructions may be executed by one or more processors to support one or more aspects of the functionality described in this disclosure.

Again referring to FIG. 9, control electronics 230 are operably coupled to input apparatus 240. Input apparatus 240 may include a switch, an antenna, a circuit, or any other suitable components that allow input indicative of a side effect to be communicated to control electronics 230. A patient, a caregiver, a healthcare provider, or the like may communicate to device 200 that the patient is experiencing a side effect from the medicament via input apparatus 240.

Figure 10:
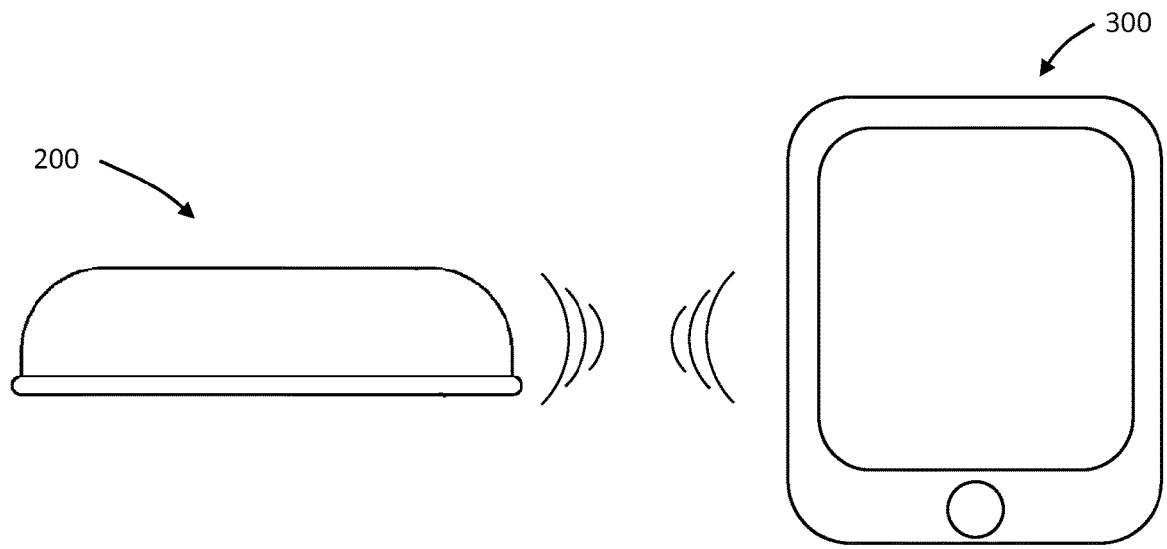
FIG. 10 is a schematic diagram of an embodiment of a medical infusion device and an auxiliary device.

Referring now to FIG. 10, input indicative of a side effect may be received by infusion device 200 from auxiliary device 300 in communication with infusion device 200. Auxiliary device 300 may be in wireless communication with infusion device 200 (e.g., via input apparatus 240 depicted in FIG. 9) as depicted, or may be wired to infusion device 200 via a cable (not shown). Auxiliary device 300 may communicate with infusion device 200 via telemetry, via the internet, or any other suitable wireless or wired communication format. Auxiliary device 300 may be controlled by a patient, a caregiver, a healthcare provider or the like. External device 300, in some embodiments, may be used to transmit instructions regarding the titration scheme to be employed, the maximum dosage, etc. Any suitable auxiliary device 300, such as a physician programmer, patient programmer, computer, mobile phone such as a smart phone, personal data assistant, tablet, or the like, may be used to communicate with infusion device 200.

Auxiliary device 300 may communication with more than one infusion device. In embodiments, auxiliary device 300 may assist two or more infusion devices in carrying out titration or therapy schemes described herein. For example, auxiliary device 300 may be in communication with a multiple infusion devices where coordinated therapy or coordinated titration are needed or desired. Control electronics (e.g., as described above) of the auxiliary device may carry out one or more aspects of the methods or schemes. For example, auxiliary device 300 may receive data regarding infusion rates of one or more infusion device and transmit instructions to the infusions devices regarding appropriate rates for coordinated delivery or titration.

Figure 11:
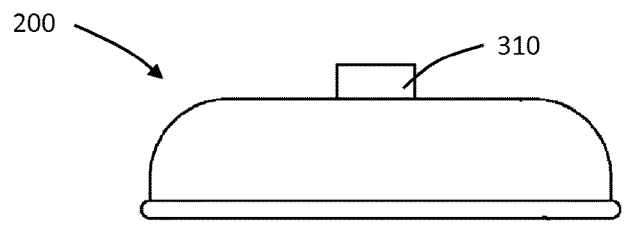
FIG. 11 is a schematic diagram of an embodiment of a medical infusion device having an input element.

Referring now to FIG. 11, infusion device 310 may have an associated input element 310 as part of input apparatus for inputting data regarding a side effect. Input element 310 may be in the form of a press button as depicted, lever, dial or any other suitable mechanism for indicating that a patient is experiencing a side effect, the severity or nature of a side effect, or the like. For example a button may be pressed once for a less severe side effect and more than once for a more severe side effect. Similarly, a dial may be turned to indicate side effect severity or nature of side effect.

Regardless of the input mechanism, communication regarding a side effect may include data regarding whether a side effect occurred, severity of side effect, nature of the side effect, or the like. Control electronics of an infusion device may use the data indicative of a side effect to control the rate at which pump mechanism delivers fluid from the reservoir to the patient according to a titration algorithm programmed into control electronics.

In some embodiments, more than one infusion device may be used to deliver therapy to a patient during a titration scheme. As indicated above with regard to FIGS. 7-8, more than one device may be employed simultaneously to deliver a medicament to a patient. However, one infusion device at a time is often used. For example, two patch pumps for delivering medicament subcutaneously via a cannula to a patient, with one of the two patch pumps being used at a given time. The location of patch pumps are periodically (e.g., about every three days) moved to avoid skin complications. After a first patch pump is used for an intended period of time, the pump, or a portion thereof, may be removed from the patient and placed on a charger. A second pump, or portion thereof, may be removed from a charger and placed on the patient at a location different from the first pump. Each pump may be used one or more times during a titration period.

In embodiments, two or more infusion devices (regardless of the type of infusion device) are synchronized when the devices are used sequentially during a titration period to allow continuous or continued titration when the infusion devices are swapped or sequentially used. Each device may be programmed with instructions regarding the overall titration scheme. When a second device is used to deliver therapy following use of a first device, the first device may transmit data regarding the last infusion rate and whether input indicative of a patient side effect was received. The second device may then pick up the titration protocol at the point the first device left off or use the data transmitted from the first device to begin the titration protocol as appropriate based on the transmitted data. Any suitable form of communication; e.g., wireless, wired, internet, etc., may be employed to communicate between the two or more devices.

Figure 12:
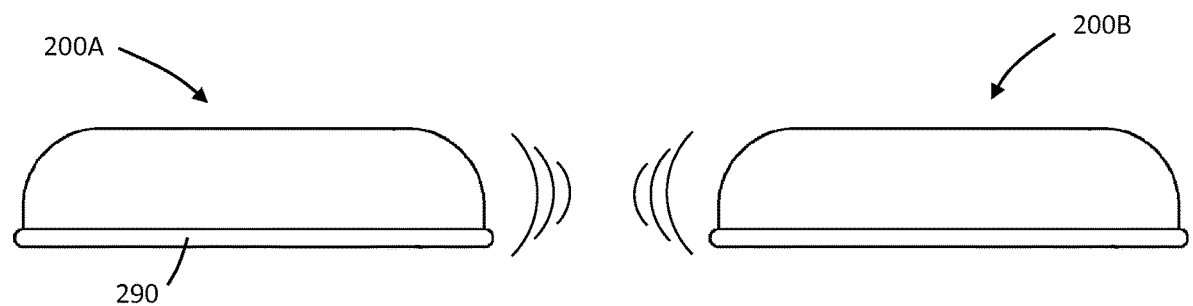
FIG. 12 is a schematic diagram of an embodiment of two medical infusion devices.

Referring now to FIG. 12, a first 200A and second 200B infusion device are shown in communication with each other by way of example. The devices 200A, 200B may be patch pumps having an adhesive layer 290 for attaching to a patient's skin. Of course, any other suitable types of infusion devices may communicate with the other to allow continuation of a titration protocol.

The methods, systems and devices described herein may be used to deliver any suitable therapy to a patient. Any suitable liquid composition comprising any suitable medicament may be delivered to a patient in accordance with a titration protocol described herein. For purposes of example, a brief discussion of delivery of an injectable ropinirole is discussed below as a prophetic example to illustrate how an orally delivered medication may be used with an infusion device, which, in this case, is an infusion device configured to deliver a medicament subcutaneously, such as a patch pump.

Isotonic, citrate-buffered (pH about 4.5), injectable solution that contains 15 mg/ml ropinirole hydrochloride may be delivered subcutaneously via a patch pump at a maximum rate of 1 ml/day. Such an injectable ropinirole solution may be a solution as described in U.S. patent application Ser. No. 13/828,148, entitled "Injectable Ropinirole Compositions and Methods for Making and Using Same," filed on Mar. 14, 2013, which patent application is hereby incorporated herein by reference in its entirety. A 1 ml/day maximum delivery rate is due to skin irritations that are known to develop with higher injection rates of other medicaments. The 15 mg/ml ropinirole solution was chosen based on the assumed 1 ml maximum daily volume and known oral maximum suggested dosages of ropinirole.

The maximum recommended daily dose of oral ropinirole is 24 mg/day. However, only about 55% of this does is systemically available because of the hepatic first pass effect. Accordingly, 0.55×24 mg/day=13.2 mg/day. It may be possible to achieve slightly higher equivalent daily dosing with subcutaneous infusion because plasma peaks associated with oral ropinirole should be avoided with continuous subcutaneous infusion. Accordingly, a 15 mg/day (15 mg/ml at 1 ml/day) maximum allows for an extra 1.8 mg/day for subcutaneous delivery.

Table 1 provides an example of a dosing conversion table for ropinirole for oral to subcutaneous dosing.

TABLE 1

Dosing Conversion Table

| Time (weeks) | Titration Dosing (mg/day) | | Daily SQ volume (mcl) to get equivalent oral dose (15 mg/ml) | Daily SQ volume if 5 mg/ml |
|---|---|---|---|---|
| | Oral | SQ | | |
| 1 | 0.75 | 0.41 | 27.3 | 82 |
| 2 | 1.5 | 0.83 | 55.3 | 166 |
| 3 | 2.25 | 1.24 | 82.7 | 248 |
| 4 | 3.0 | 1.65 | 110.0 | 330 |
| 5 | 4.5 | 2.48 | 165.3 | 496 |
| 6 | 6.0 | 3.30 | 220.0 | 660 |
| 7 | 7.5 | 4.13 | 275.3 | 826 |
| 8 | 9.0 | 4.95 | 330.0 | 990 |
| 9 | 12 | 6.60 | 440.0 | 1320* |
| 10 | 15 | 8.25 | 550.0 | 1650 |
| 11 | 18 | 9.90 | 660.0 | 1980 |
| 12 | 21 | 11.55 | 770.0 | 2310** |
| 13 | 24 | 13.20 | 880.0 | 2640 |

As indicated by the * and ** the maximum desired daily subcutaneous (SQ) volume (1 ml/day) would be exceeded at the 12 mg/day daily dose equivalent if a 5 mg/ml injectable ropinirole solution were used and the maximum desired daily volume (1 ml/day) would be exceeded at the 21 mg/day daily dose equivalent if a 10 mg/ml injectable ropinirole solution were used. Accordingly, a 15 mg/ml injectable ropinirole solution may be most desirable for those patients that can tolerate higher doses.

Thus, embodiments of TITRATION FOR MEDICAL INFUSION DEVICES AND SYSTEMS are disclosed. One skilled in the art will appreciate that the apparatuses, systems and methods described herein can be practiced with embodiments other than those disclosed. The disclosed embodiments are presented for purposes of illustration and not limitation. One will also understand that components of the apparatuses, systems and methods depicted and described with regard to the figures and embodiments herein may be interchangeable.

Use of "first," "second," etc. in the description above and the claims that follow is not intended to necessarily indicate that the enumerated number of objects are present. For example, a "second" infusion is merely intended to differentiate from another infusion device (such as a "first" infusion). Use of "first," "second," etc. in the description above and the claims that follow is also not necessarily intended to indicate that one comes earlier in time than the other.

The invention claimed is:

1. A medical infusion system comprising:
a first device having first control electronics and having, or configured to operably couple to, (i) a first reservoir for housing a liquid composition comprising a medicament, (ii) a first pump mechanism configured to drive the liquid composition from the first reservoir to a patient, and (iii) a first input apparatus configured to receive input indicative of a patient side effect of the medicament, wherein the first control electronics are operably coupled to the first pump mechanism and to the first input apparatus, and wherein the first control electronics are configured:

(a) to cause the first pump mechanism to drive the liquid composition from the first reservoir to the patient for a first predetermined period of time at a rate increased relative to a first preceding rate if no input indicative of the patient side effect has been received during a period of time in which the first pump mechanism drove the liquid composition from the first reservoir to the patient at the first preceding rate; and (b) to repeat step (a) until a maximum predetermined rate has been achieved or until input indicative of the patient side effect is received; and a second device having second control electronics and having, or configured to operably couple to, (i) a second reservoir for housing amount of the liquid composition comprising the medicament, (ii) a second pump mechanism configured to drive the liquid composition from the second reservoir to the patient, and (iii) a second input apparatus configured to receive input indicative of the patient side effect of the medicament, wherein the second control electronics are operably coupled to the second pump mechanism and to the second input apparatus, and wherein the second control electronics are configured:

(c) to cause the second pump mechanism to drive the liquid composition from the second reservoir to the patient for a second predetermined period of time at a rate increased relative to a second preceding rate if no input indicative of the patient side effect has been received during a period of time in which the second pump mechanism drove the liquid composition from the second reservoir to the patient at the second preceding rate; and (d) to repeat step (c) until a maximum predetermined rate has been achieved or until the second control electronics determine that input indicative of the patient side effect is received, wherein the first and second pump mechanisms are the same or different, wherein the first and second reservoirs are the same or different, wherein the first and second input apparatuses are the same or different, and wherein the first and second devices are configured to be employed by the patient sequentially such that the second device is employed by the patient to deliver the medicament after the first device is no longer being used to deliver the medicament, and wherein the first device is configured to transmit to the second device data regarding a last rate at which the first pump mechanism was configured to drive the liquid composition from the first reservoir to the patient, and wherein the second control electronics are configured to set the last rate of the first pump mechanism as the initial rate of the second pump mechanism in step (c).

2. The medical infusion system of claim 1, wherein, if input indicative of the patient side effect is received, the first control electronics are further configured to cause the first pump mechanism to drive the liquid composition from the first reservoir to the patient at a rate decreased relative to a rate in a time period in which the input indicative of the patient side effect was received.

3. The medical infusion system of claim 1, wherein, if input indicative of the patient side effect is received, the second control electronics are further configured to cause the second pump mechanism to drive the liquid composition from the second reservoir to the patient at a rate decreased relative to a rate in a time period in which the input indicative of the patient side effect was received.

4. The medical infusion system of claim 1, wherein the first device is configured to transmit to the second device data regarding whether input indicative of the patient side effect has been received.

5. The medical infusion system of claim 4, wherein the second control electronics are configured to cause the second pump mechanism to drive the liquid composition at the last rate of the first pump mechanism without increasing the rate in the step (c) if the second device receives data from the first device indicating that the first apparatus received input indicative of the patient side effect.

6. The medical infusion system of claim 1, wherein the first and second devices are ambulatory devices.

7. The method of claim 1, wherein the first device is a first patch pump, and wherein the second device is a second patch pump.

8. A method of titrating dosage of a medicament from a medical infusion system sequentially employing first and second devices to deliver the medicament to a patient such that the second device replaces the first device to deliver the medicament to the patient after the first device is no longer employed to deliver the medicament, the method comprising:

(1) employing control electronics of the first device to:
  (a) determine whether an input indicative of the patient side effect has been received;
  (b) cause a liquid composition comprising the medicament to be delivered to a patient for a first predetermined period of time at a rate increased relative to a first preceding rate if a determination is made that no input indicative of the patient side effect has been received during a period of time in the liquid composition was driven at the first preceding rate; and
  (c) repeat steps (a) and (b) until a maximum predetermined rate has been achieved or until the determination is made that input indicative of the patient side effect has been received or until the first device is replaced by the second device; and (2) replacing the first device with the second device, transmitting data to the second device regarding a last rate at which the first device caused the liquid composition to be delivered to the patient, and transmitting data to the second device regarding whether input indicative of the patient side effect has been received; and (3) employing control electronics of the second device to:
  (d) cause the liquid composition comprising the medicament to be delivered to the patient at the last rate at which the first device caused the liquid composition to be delivered to the patient if the transmitted data indicates that the maximum predetermined rate has been achieved or that input indicative of the patient side effect has been received; or
  (e) if the transmitted data indicates that the maximum predetermined rate has not been achieved and that no input indicative of the patient side effect has been received,
    (i) cause the liquid composition comprising the medicament to be delivered to the patient for a second predetermined period of time at the last rate at which the first device caused the liquid composition to be delivered to the patient or a rate increased relative to the last rate at which the first device caused the liquid composition to be delivered to the patient;

(ii) determine whether input indicative of the patient side effect has been received;

(iii) cause the liquid composition comprising the medicament to be delivered to the patient for a third predetermined period of time at a rate increased relative to a third preceding rate if a determination is made that no input indicative of the patient side effect has been received during a period of time in the liquid composition was driven at the third preceding rate; and (a) (iv) repeat steps (ii) and (iii) until the maximum predetermined rate has been achieved or until the determination is made that input indicative of the patient side effect has been received.

9. The method of claim 8, wherein the first device is a first patch pump, and wherein the second device is a second patch pump.

10. A method for titrating dosage of a medicament from a medical system employing first and second infusion devices to deliver the medicament to a patient, wherein the system optionally comprises an auxiliary device in communication with the first and second infusion devices, the method carried out by (i) the first and second infusion devices or (ii) the first and second infusion devices and the auxiliary device and comprising:

(a) infusing a first liquid composition comprising the medicament from the first infusion device to the patient;

(b) infusing a second liquid composition comprising the medicament from the second infusion device to the patient;

(c) determining the combined rate of infusion from the first device and the second device;

(d) determining whether a maximum combined rate has been achieved;

(e) determining whether input indicative of a patient side effect has been received;

(f) infusing the first and second liquid compositions from the first and second devices for a predetermined period of time at a predetermined combined rate increased relative to a combined preceding rate if a determination is made that no input indicative of the patient side effect has been received during a period of time in which the first and second devices drove the first and second liquid compositions to the patient at the preceding combined rate and if the maximum combined rate has not been achieved; and (g) repeating steps (d) through (f) until a maximum predetermined combined rate has been achieved or until a determination is made that input indicative of the patient side effect has been received.

11. The method of claim 10, further comprising:

(h) increasing a first rate of infusion from the second device and decreasing a second rate of infusion from the first device to maintain a combined infusion rate;

(i) determining whether the first infusion device is infusing the first liquid composition at a rate below a predetermined threshold;

(j) repeating steps (h) and (i) until the first infusion device is infusing the first liquid composition below the threshold; and (k) removing the first infusion device from the patient if the first device is infusing the first liquid composition below the threshold.

12. The method of claim 10, wherein the first infusion device is a first patch pump, and wherein the second infusion device is a second patch pump.

* * * * *